(12) United States Patent
Tope

(10) Patent No.: US 8,586,537 B2
(45) Date of Patent: Nov. 19, 2013

(54) METHOD FOR TREATING MINOR APHTHOUS ULCERS

(76) Inventor: Rick Tope, North Las Vegas, NV (US)

( * ) Notice: Subject to any disclaimer, the term of this patent is extended or adjusted under 35 U.S.C. 154(b) by 1935 days.

(21) Appl. No.: 11/420,376

(22) Filed: May 25, 2006

(65) Prior Publication Data

US 2007/0275056 A1 Nov. 29, 2007

(51) Int. Cl.
*A61K 38/00* (2006.01)
*A61K 8/21* (2006.01)

(52) U.S. Cl.
USPC .............................. 514/13.2; 514/904; 424/52

(58) Field of Classification Search
None
See application file for complete search history.

(56) References Cited

U.S. PATENT DOCUMENTS

| | | | | |
|---|---|---|---|---|
| 3,171,782 | A | * | 3/1965 | Fellonneau ..................... 424/48 |
| 5,686,095 | A | | 11/1997 | Price, Jr. |
| 6,129,918 | A | * | 10/2000 | Amagase ...................... 424/754 |
| 6,255,294 | B1 | * | 7/2001 | Armstrong et al. .............. 514/52 |
| 6,344,214 | B1 | | 2/2002 | Lorenz |
| 6,894,033 | B2 | | 5/2005 | Cruz et al. |
| 2004/0156930 | A1 | | 8/2004 | Haley |
| 2005/0163751 | A1 | | 7/2005 | Cruz et al. |
| 2005/0175585 | A1 | | 8/2005 | Cruz et al. |
| 2005/0240085 | A1 | * | 10/2005 | Knoell et al. ................. 600/300 |
| 2007/0269526 | A1 | * | 11/2007 | Bos et al. ....................... 424/502 |

OTHER PUBLICATIONS

Austin Research, What is the Right 'Dosage' for Vitamin B6, DMG, and Other Nutrients Useful in Autism?, Autism Research Review International, 1997, vol. 11, No. 4, p. 3.*
Rogers, Recurrent Aphthous Stomatitis: Clinical Characteristics and Associated Systemic Disorders; W.B. Saundrs Company Seminars in Cutaneous Medicine and Surgery, vol. 16, No. 4 Dec. 1997: pp. 278-283.*
Scully et al., IgE and IgD concentrations in patients with recurrent aphthous, Arch Dermatol. Jan. 1983; 119(1): 31-4.*
Barnes et al., Drug Dosage in Laboratory Animals, A Handbook, University of California Press, Third printing 1966, p. 2.*
Volkov et al. "Case report: Recurrent aphthous stomatitis responds to vitamin B12 treatment", Le Medecin de famille canadien, vol. 51:Jun. 2005.*
Robert S. Rister, 2003, Healing Without Medication: A comprehensive Guide to the Complementary Techniques Anyone Can Use to Achieve Real Healing, Basic Health Publications Inc. USA.*
Mark et al., The Vascular Toxicity of Homocysteine and How to Control It, The Linus Pauling Institute Newsletter, Fall/Winter 1999.*
Nolan et al., Recurrent aphthous ulceration: vitamin B1, B2, and B6 status and response to replacement therapy, J Oral Pathol. Med 1991; 20:389-91.*
Mehmet et al., Plasma Homocysteine Level and Uveitis in Behcet's disease, IMAJ 2002;4(Suppl):931-934.*
Harvard School of Public Health document, The Nutrition Source—How Much Do I need? Vitamin B12.*

* cited by examiner

*Primary Examiner* — Michael G Hartley
*Assistant Examiner* — Nabila Ebrahim
(74) *Attorney, Agent, or Firm* — Weiss & Moy, P.C.; Veronica-Adele R. Cao

(57) ABSTRACT

A method for treating recurrent minor aphthous ulcers is provided in which a sufferer is treated with a combination therapy of Vitamin B6 and B12 compounds. The treatment is done orally and the treatment minimizes the duration and pain of the sore, as well as increasing the period of time between recurrences.

14 Claims, No Drawings

METHOD FOR TREATING MINOR APHTHOUS ULCERS

FIELD OF THE INVENTION

This invention relates to a method of treating recurrent minor aphthous ulcers by oral administration of a natural composition to limit their duration, lessen the pain and discomfort they cause and to reduce their recurrence.

BACKGROUND OF THE INVENTION

Recurrent minor aphthous ulcers (of which canker sores are one type) are painful ulcers that develop inside the mouth. Canker sores are distinguished from other mouth ulcers by way of taking a history from a patient and by way of visual inspection. Typically there is no medical testing (i.e., biopsy or culturing) that is used to identify canker sores.

The hallmark characteristics of canker sores are their appearance, location, and the fact that they are recurrent. Canker sores form on the inside of the lips and cheeks, the floor of the mouth, the tongue, the soft palate, the tonsillar areas, and other areas in the mouth. The tissues surrounding a canker sore lesion will appear healthy and the patient will have no distinguishing systemic features (such as a fever or malaise).

A canker sore's earliest stage will be characterized by the formation of a reddish area on the skin in one of the locations described above. The area may be slightly elevated and it will often produce a tingling sensation. This initial lesion will subsequently degenerate into an ulcer that is round or oval in shape. The ulcer will usually be no more than a ¼ inch in diameter. The center of the ulcer will be covered with a loosely attached white or grayish membrane. The edges of the ulcer will be regular (not jagged) and surrounded by a reddish halo.

Canker sores usually are painful. It is common that the presence of a canker sore will interfere with eating and drinking or will cause a person to want to limit their oral movements. Canker sores normally last from ten days to two weeks. Usually this healing is uneventful with no residual scarring.

Once a person has initially experienced an outbreak of canker sores, the probability of recurrence is high, although the rate of recurrence is quite variable. A rate of one or two outbreaks per year would be considered typical (encompassing 50% of those who get canker sores). 30% of people who suffer from outbreaks of these lesions deal with their presence on a monthly basis. The number of outbreaks of canker sores a person experiences can vary greatly. Most persons will have only a few episodes a year while, at the other extreme, others will have nearly continuous outbreaks and will never be free of mouth ulcers for an extended period of time. A person's first canker sores typically appear between the ages of 10 and 20 years and then decrease in frequency and severity as the person ages. It's been estimated that roughly 20% of the general population experiences canker sores.

The precise mechanism by which canker sores form has not been definitively determined but it is likely that their development is related to a reaction of an individual's own immune system. Several triggers for canker sores have been identified.

Treatments for canker sores have included over the counter and prescription products. Such products include those which create a protective barrier film, those that numb the canker sore, etc. However, these products do not speed up the healing; they simply cover over and protect them. Antibacterial products may be used to prevent secondary infections from forming in the lesions. Anti-inflammatory medicines can help to minimize the extent to which a canker sore's ulceration will progress. Unfortunately, none of these treatments have proven particularly effective to speed healing, relieve pain, and reduce the frequency of recurrent minor aphthous ulcers, including canker sores.

Vitamin B12 is a cobalt-containing B complex vitamin that has various effects on biological processes in vivo. The majority of people do not need to take vitamin B12 supplements, however, vitamin B12 compounds have been available for many years as an injectable treatment for pernicious anemia, with daily doses typically in the range of 1000 micrograms. Vitamin B12 supplements are also known in the microgram range.

Vitamin B6 plays a role in a variety of biochemical reactions in the human body including the metabolism of amino acids and glycogen, the synthesis of nucleic acids, hemoglobin, sphingomyelin and other sphingolipids, and the biosynthesis of neurotransmitters including serotonin, dopamine, norepinephrine, and gamma-aminobutyric acid (GABA). Vitamin B6 is the primary vitamin for processing amino acids used in production of proteins and is also needed to make a variety of hormones including serotonin, melatonin, and dopamine. Typical doses of pyridoxine used for nutritional supplementation range from 2 to 20 milligrams/day.

Though Vitamin B6 in combination with folic acid and vitamin B12 have been known to control homocysteine levels which have been linked to heart disease, stroke, osteoporosis and Alzheimer's disease, no person has demonstrated that high doses of a vitamin B6 compound in combination with a vitamin B12 compound would achieve an enhanced therapeutic effect for the treatment of recurrent minor aphthous ulcers.

Accordingly, there has been a need for a novel method of treating minor aphthous ulcers which is safe and substantially effective at limiting their duration, lessening the pain and discomfort they cause, and reducing their recurrence. The present invention fulfills these needs and provides other related advantages.

SUMMARY OF THE INVENTION

The present invention relates to a method for treating recurrent minor aphthous ulcers, comprising the step of orally administering to a patient, either together or separately, at least one vitamin B12 compound and at least one vitamin B6 compound.

Other features and advantages of the present invention will become apparent from the following more detailed description.

DETAILED DESCRIPTION OF THE PREFERRED EMBODIMENTS

The present invention is concerned with a method for treating recurrent minor aphthous ulcers comprising the step of orally administering to a patient, either together, or separately, at least one vitamin B12 compound and at least one vitamin B6 compound.

"Vitamin B12 compounds" as used herein means a class of compounds which includes vitamin B12 and its analogues, derivatives or conjugates. The class of vitamin B12 compounds includes cyanocobalamin (CN-Cbl), aquacobalamin, adenosylcobalamin, methylcobalamin, hydroxycobalamin (HC), cyanocobalamin carbanalide, and 5-o-methylbenzyl-cobalmin [(5-OmeB-za)CN-Cbl] as well as the desdimethyl, monoethylamide and the methylamide analogues of all of the above. Also included are the various analogues and homologues of cobamamide such as coenzyme B12 and 5-deoxy-denosylcobalamin. Other analogues include chlorocobalamin, sulfitocobalamin, nitrocobalamin, thiocyanatocobalamin, benzimidazole derivatives such as 5,6-dichlorobenzimidazole, 5-hydroxybenzimidazole, trimethylbenzimidazole, as well as adenosylcyanocobalamin [(Ade)CN-Cbl], cobalamin lactone, cobalamin lactam and the anilide, ethylamide, monocarboxylic and dicarboxylic acid derivatives of vitamin B12 or its analogues. Preferred derivatives of vitamin B12 include the mono-, di- and tricarboxylic acid derivatives or the proprionamide derivatives of vitamin B12. In addition, the compositions include polymers of these analogues or vitamin B12 conjugated to other molecules or encapsulated. The singular form, "vitamin B12 compound", means any one or more compounds from the class of vitamin B12 compounds. The preferred form of vitamin B12 is cyanocobalamin (CN-Cbl) available from Vitamin World, Ronkonkoma, N.Y.

"Vitamin B6 compounds" means pyridoxine, pyridoxal, pyridoxomaxine, their phosphorylated derivatives pyridoxine 5'-phosphate, pyridoxal 5'-phosphate, and pyridoxamine 5'-phosphate. Vitamin B6 is a group of the three related compounds pyridoxine, pyridoxal, and pyridoxamine, their phosphorylated derivatives pyridoxine 5'-phosphate, pyridoxal 5'-phosphate and pyridoxamine 5'-phosphate. The preferred vitamin B6 compound is Pyridoxine hydrochloride available from Vitamin World, Ronkonkoma, N.Y.

The amount of active compound in such therapeutically useful compositions or preparations is such that a suitable dosage will be obtained. The dose of vitamin B6 compound may be about ten times the dose of vitamin B12 compound for both treatment and maintenance doses. "Treatment dose" as used herein means the dose necessary to treat an existing ulcer to reduce its duration and pain. "Maintenance dose" as used herein means the dose taken to prevent an ulcer.

Suitable approximate treatment dosages may be as follows:

|  | B6 | B12 |
| --- | --- | --- |
| Range | 2-6 mg/kg body weight | .2-.6 mg/kg body weight |
| Preferred | 4 mg/kg body weight | .4 mg/kg body weight |
| Daily Maximum | 2000 mg | 2 grams (2000 mg) |
| Daily Minimum | 50 mg | 5 mg |

Suitable approximate maintenance doses may be as follows:

|  |  |  |
| --- | --- | --- |
| Range | 2-3 mg/kg body weight | .2-.3 mg/kg body weight |
| Preferred | 2 mg/kg body weight | .2 mg/kg body weight |
| Daily Maximum | 1000 mg | 1000 mg |
| Daily Minimum | 2 mg/kg body weight | .2 mg/kg body weight |

The maximum dosage for the vitamin B6 compound reflects the maximum that a patient can tolerate over an extended period of time and not develop serious complications.

The combination of the vitamin B6 compound with the vitamin B12 compound provides enhanced effectiveness at treating recurrent minor aphthous ulcers. The term "enhanced effectiveness" means an enhanced therapeutic effect, and includes a synergistic effect. "Synergistic" means a greater effect with the use of a combination therapy of vitamin B12 and vitamin B6 compound than with the use of any of these therapeutic compounds alone. One advantage of a combination therapy with a synergistic effect is that standard dosages can be used for a greater therapeutic effect than expected from the addition of the effect of either compound administered alone; or alternatively lower dosages or reduced frequency of administration of the therapeutic compound (s) may be used to achieve a better therapeutic effect.

The compounds of the present invention in the described dosages are administered orally including sublingually. For oral administration the pharmaceutical composition can be prepared, for example, in the form of tablets, troches, capsules, elixirs, suspensions, syrups, wafers, chewing gum or the like prepared by procedures known to those skilled in the art.

The first method of treatment is the administration of a composition including both a vitamin B12 compound and a vitamin B6 compound. An alternate method of treatment includes the step of administration of a composition including a vitamin B12 compound followed by the step of the administration of a second pharmaceutical composition including the vitamin B6 compound or vice versa. The administration of the compositions can occur separately or in combination. If the B6 and B12 compositions are taken separately, administration should be substantially simultaneous. The frequency of administration is preferably once daily.

Reference will now be made to specific examples of the methods described above. It is to be understood that the examples are provided to more completely describe the preferred embodiments and that no limitation to the scope of the invention is intended thereby.

EXAMPLE 1

A 5 year old female weighing 42 pounds (19 kg) was given a dose of 10,000 micrograms (10 mg) B12 and 100 mg B6 daily starting 3-4 days after onset. The pain disappeared by the next day and the sores were totally gone in two more days.

EXAMPLE 2

A 12 year male weighing 86 pounds (39 kg) was orally administered the same dose within 12 hours after the sore developed. The sore was totally gone the next day.

EXAMPLE 3

A female weighing 135 pounds (61 kg) had a canker sore for one week when she was administered a dose of 15 mg vitamin B12 compound and 150 mg vitamin B6 compound. The sore was gone the next day.

EXAMPLE 4

A male weighing 165 pounds (75 kg) had a canker sore for one week when he was administered 10 mg vitamin B12 compound and 100 mg vitamin B6 compound. This had no effect. The next day, he was administered 15 mg vitamin B12 compound and 150 mg vitamin B6 compound. This dose also had no effect. In addition, he was starting to form another sore. He was then administered 30 mg vitamin B12 compound and 300 mg vitamin B6 compound. By the next day, the original sore was gone and the pain had disappeared from the new sore. After two more days of treatment, the new sore was gone.

Maintenance Dose

EXAMPLE 5

A male weighing 173 pounds (78 kg) took a daily dose of 15 mg vitamin B12 compound and 150 mg vitamin B6 compound to substantially prevent the recurrence of canker sores.

From the foregoing, it is to be appreciated that high doses of a vitamin B6 compound in combination with a vitamin B12 compound achieves an enhanced therapeutic effect for the treatment of recurrent minor aphthous ulcers.

Although a particular embodiment of the invention has been described in detail for purposes of illustration, various modifications may be made without departing from the spirit and scope of the invention. Accordingly, the invention is not to be limited, except as by the appended claims.

I claim:

1. A method of treating recurrent minor aphthous ulcers comprising the step of orally administering to a patient in need thereof (a) at least one vitamin B12 compound and (b) at least one vitamin B6 compound wherein a once daily treatment dose of the at least one vitamin B12 compound is dependent upon a body weight of a patient and is between about 0.2-0.6 mg/kg body weight, wherein a treatment dose of the at least one vitamin B6 compound is dependent upon the body weight of the patient and is between about 2.0 mg/kg body weight and 6.0 mg/kg body weight and wherein the at least one vitamin B12 compound and the at least one vitamin B6 compound are contained in a pharmaceutical composition and wherein said administration causes the aphthous ulcers to disappear within between one and three days.

2. The method of claim 1, wherein the treatment dose of the at least one vitamin B12 compound is about 0.4 mg/kg body weight and the treatment dose of the at least one vitamin B6 compound is about 4 mg/kg body weight.

3. The method of claim 1 further comprising the step of orally administering to the patient after existing aphthous ulcers have disappeared a once daily maintenance dose to decrease the frequency and the severity of ulcers, wherein the maintenance dose of the at least one vitamin B12 compound is between about 0.2 to about 0.3 mg/kg body weight and the maintenance dose of the at least one vitamin B6 compound is between about 2.0 to about 3.0 mg/kg body weight.

4. The method of claim 3, wherein the once daily maintenance dose of the at least one vitamin B12 compound is about 0.2 mg/kg and the maintenance dose of the at least one vitamin B6 compound is about 2.0 mg/kg body weight.

5. The method of claim 1, wherein the at least one vitamin B12 compound and the at least one vitamin B6 compound are taken in about a 1:10 dosage ratio.

6. A method of treating recurrent minor aphthous ulcers in patients in need thereof comprising the following steps:
   determining a once daily treatment dose of vitamin B12 for the patient that is dependent upon weight of the patient;
   determining a once daily treatment dose of vitamin B6 for the patient that is dependent upon the weight of the patient;
   orally administering to the patient the treatment dose of vitamin B12 and the treatment dose of vitamin B6 in a composition,
   wherein the administration of the treatment dose of vitamin B6 coincides with the administration of the treatment dose of vitamin B12, causing a greater therapeutic effect than when either of the treatment doses of vitamin B12 and vitamin B6 is administered alone, and causing the aphthous ulcers to disappear within between one and three days;
   determining a once daily maintenance dose of vitamin B12 for the patient that is about half of the once daily treatment dose of vitamin B12;
   determining a maintenance dose of vitamin B6 for the patient that is about half of the treatment dose of vitamin B6; and
   after existing aphthous ulcers have disappeared, orally administering to the patient the once daily maintenance dose of vitamin B12 and the once daily maintenance dose of vitamin B6 in a composition, wherein the maintenance dose of vitamin B12 and vitamin B6 are administered to decrease the frequency and the severity of the ulcers.

7. The method of claim 6, wherein the treatment dose of the at least one vitamin B12 compound is between about 0.2 mg/kg body weight and about 0.6 mg/kg body weight and the treatment dose of the at least one vitamin B6 compound is between about 2.0 mg/kg body weight and 6.0 mg/kg body weight.

8. The method of claim 7, wherein the treatment dose of the at least one vitamin B12 compound is about 0.4 mg/kg body weight and the treatment dose of the at least one vitamin B6 compound is about 4.0 mg/kg body weight.

9. The method of claim 7, wherein the maintenance dose of the at least one vitamin B12 compound is between about 0.2 mg/kg body weight to about 0.3 mg/kg body weight and the maintenance dose of the at least one vitamin B6 compound is between about 2.0 mg/kg body weight to about 3 mg/kg body weight.

10. The method of claim 8 wherein the maintenance dose of the at least one vitamin B12 compound is about 0.2 mg/kg and the maintenance dose of the at least one vitamin B6 compound is about 2.0 mg/kg body weight.

11. The method of claim 6 claim wherein the treatment dose of the at least one vitamin B12 compound and the treatment dose of the at least one vitamin B6 compound are taken in about 1:10 dosage ratio.

12. A method of treating recurrent minor aphthous ulcers comprising the steps of:
   orally administering to a patient in need thereof a once daily treatment dose of a composition including at least one vitamin B12 compound and at least one vitamin B6 compound in about a 1:10 ratio, wherein the treatment dose of the at least one vitamin B12 compound is dependent upon the body weight of the patient and wherein the treatment dose of the at least one vitamin B6 compound is dependent upon the body weight of the patient, wherein said administration causes the aphthous ulcers to disappear within between one and three days; and
   after existing aphthous ulcers have disappeared orally administering once daily to the patient another composition including at least one vitamin B12 compound and at least one vitamin B6 compound in about a 1:10 ratio to decrease the frequency and the severity of the ulcers,
   wherein a maintenance dose of the at least one vitamin B12 compound is about half of the treatment dose of the at least one vitamin B12 compound and wherein a maintenance dose of the at least one vitamin B6 compound is about half of the treatment dose of the at least one vitamin B6 compound.

13. The method of claim 12, wherein the treatment dose of the at least one vitamin B12 compound is about 0.4 mg/kg body weight and the treatment dose of the at least one vitamin B6 compound is about 4.0 mg/kg body weight.

14. The method of claim 13, wherein the maintenance dose of the at least one vitamin B12 compound is about 0.2 mg/kg and the maintenance dose of the at least one vitamin B6 compound is about 2.0 mg/kg body weight.

* * * * *